(12) United States Patent
Schlesinger et al.

(10) Patent No.: US 9,439,692 B1
(45) Date of Patent: Sep. 13, 2016

(54) MINIMALLY INVASIVE SPINAL FIXATION SYSTEM AND METHOD THEREFOR

(71) Applicant: SPINE WAVE, INC., Shelton, CT (US)

(72) Inventors: Scott M. Schlesinger, Little Rock, AR (US); John A. Pafford, Eads, TN (US)

(73) Assignee: SPINE WAVE, INC., Shelton, CT (US)

( * ) Notice: Subject to any disclaimer, the term of this patent is extended or adjusted under 35 U.S.C. 154(b) by 0 days.

(21) Appl. No.: 14/879,368

(22) Filed: Oct. 9, 2015

(51) Int. Cl.
*A61B 17/70* (2006.01)

(52) U.S. Cl.
CPC .................. *A61B 17/7082* (2013.01)

(58) Field of Classification Search
CPC ................... A61B 17/7074–17/7091
USPC .......................... 606/86 A, 99, 279
See application file for complete search history.

(56) References Cited

U.S. PATENT DOCUMENTS

| | | | |
|---|---|---|---|
| 4,411,259 A | 10/1983 | Drummond | |
| 4,927,425 A | 5/1990 | Lozier | |
| 5,242,443 A | 9/1993 | Kambin | |
| 5,540,688 A * | 7/1996 | Navas | A61B 17/7005 606/266 |
| 5,910,141 A | 6/1999 | Morrison et al. | |
| 5,984,923 A * | 11/1999 | Breard | A61B 17/7002 606/259 |
| 6,090,113 A | 7/2000 | Le Couedic et al. | |
| 6,139,549 A * | 10/2000 | Keller | A61B 17/7032 606/104 |
| 6,183,472 B1 * | 2/2001 | Lutz | A61B 17/7032 606/104 |
| 6,226,548 B1 | 5/2001 | Foley et al. | |
| 6,235,028 B1 | 5/2001 | Brumfield et al. | |
| 6,530,929 B1 | 3/2003 | Justis et al. | |
| 6,648,888 B1 | 11/2003 | Shluzas | |
| 6,743,231 B1 | 6/2004 | Gray et al. | |
| 6,802,844 B2 | 10/2004 | Ferree | |
| 6,916,330 B2 | 7/2005 | Simonson | |
| 7,008,422 B2 | 3/2006 | Foley et al. | |
| 7,008,431 B2 | 3/2006 | Simonson | |
| 7,011,660 B2 | 3/2006 | Sherman et al. | |
| 7,179,261 B2 | 2/2007 | Sicvol et al. | |
| 7,188,626 B2 | 3/2007 | Foley et al. | |
| 7,250,052 B2 | 7/2007 | Landry et al. | |
| 7,306,603 B2 | 12/2007 | Boehm, Jr. | |
| 7,473,269 B1 | 1/2009 | Hynes | |
| 7,476,240 B2 | 1/2009 | Raymond et al. | |
| 7,491,218 B2 | 2/2009 | Landry et al. | |

(Continued)

OTHER PUBLICATIONS

Synthes Constellation CP Surgical System Technique Guide, © 2007 Synthes, Inc., West Chester, PA.

(Continued)

*Primary Examiner* — Eduardo C Robert
*Assistant Examiner* — Michelle C Eckman
(74) *Attorney, Agent, or Firm* — Hoffman & Baron, LLP

(57) ABSTRACT

A minimally invasive spinal fixation system comprises first and second bone screws each including a threaded shaft for respective engagement with a vertebra and a yoke articulatingly attached to the shaft, each yoke including a pair of upstanding opposed arms defining a slot therebetween. A connecting element has opposite ends and a longitudinal axis extending therebetween, the connecting element including a tab adjacent each end projecting from the connecting element transversely to the longitudinal axis. Bone screw extensions are provided for guiding the placement of the connecting element into the yoke slots, each extension having a pair of opposing slots that are sized to pass the tabs through the extensions when oriented in a first position and to prevent passage when the tabs are oriented in a second different position.

11 Claims, 9 Drawing Sheets

(56) References Cited

U.S. PATENT DOCUMENTS

| | | | |
|---|---|---|---|
| 7,520,879 B2 | 4/2009 | Justis et al. | |
| 7,527,638 B2 | 5/2009 | Anderson et al. | |
| 7,547,318 B2 | 6/2009 | Birkmeyer et al. | |
| 7,563,264 B2 | 7/2009 | Landry et al. | |
| 7,572,276 B2 | 8/2009 | Lim et al. | |
| 7,597,694 B2 | 10/2009 | Lim et al. | |
| 7,666,188 B2 | 2/2010 | Anderson et al. | |
| 7,666,211 B2 | 2/2010 | Perez-Cruet et al. | |
| 7,691,132 B2 | 4/2010 | Landry et al. | |
| 7,708,763 B2 | 5/2010 | Selover et al. | |
| 7,914,552 B2 | 3/2011 | Shelton, IV | |
| 7,922,725 B2 * | 4/2011 | Darst Rice | A61B 17/8869 606/254 |
| 7,927,356 B2 | 4/2011 | Lim | |
| 7,927,360 B2 | 4/2011 | Pond, Jr. et al. | |
| 7,985,242 B2 | 7/2011 | Forton et al. | |
| 8,034,084 B2 | 10/2011 | Landry et al. | |
| 8,075,592 B2 | 12/2011 | Landry et al. | |
| 8,142,437 B2 | 3/2012 | McLean et al. | |
| 8,303,628 B2 | 11/2012 | Dewey et al. | |
| 8,439,924 B1 * | 5/2013 | McBride | A61B 17/708 606/104 |
| 8,496,685 B2 | 7/2013 | Landry et al. | |
| 8,523,916 B2 | 9/2013 | Anderson et al. | |
| 8,636,740 B2 * | 1/2014 | Weaver | A61B 17/025 606/104 |
| 8,721,692 B2 | 5/2014 | Anderson et al. | |
| 8,828,005 B2 | 9/2014 | Birkmeyer et al. | |
| 8,834,527 B2 | 9/2014 | Hutton et al. | |
| 8,956,362 B2 | 2/2015 | Landry et al. | |
| 2004/0039384 A1 * | 2/2004 | Boehm, Jr. | A61B 17/1757 606/86 A |
| 2004/0138662 A1 * | 7/2004 | Landry | A61B 17/1604 606/86 A |
| 2005/0080418 A1 | 4/2005 | Simonson et al. | |
| 2005/0085813 A1 * | 4/2005 | Spitler | A61B 17/1757 606/86 A |
| 2005/0131408 A1 * | 6/2005 | Sicvol | A61B 17/7091 606/86 A |
| 2005/0131421 A1 * | 6/2005 | Anderson | A61B 17/7074 606/99 |
| 2005/0154389 A1 | 7/2005 | Selover et al. | |
| 2005/0192589 A1 * | 9/2005 | Raymond | A61B 17/7002 606/99 |
| 2005/0215999 A1 * | 9/2005 | Birkmeyer | A61B 17/7005 606/914 |
| 2005/0245928 A1 * | 11/2005 | Colleran | A61B 17/708 606/90 |
| 2006/0036244 A1 * | 2/2006 | Spitler | A61B 5/103 74/1 R |
| 2006/0069391 A1 * | 3/2006 | Jackson | A61B 17/7037 606/62 |
| 2006/0084993 A1 | 4/2006 | Landry et al. | |
| 2006/0111714 A1 * | 5/2006 | Foley | A61B 17/1671 606/279 |
| 2006/0247630 A1 * | 11/2006 | Iott | A61B 17/701 606/86 A |
| 2007/0049931 A1 * | 3/2007 | Justis | A61B 17/7089 606/86 A |
| 2007/0191840 A1 * | 8/2007 | Pond | A61B 17/7085 623/17.16 |
| 2007/0233097 A1 * | 10/2007 | Anderson | A61B 17/7079 606/86 A |
| 2007/0288026 A1 * | 12/2007 | Shluzas | A61B 17/02 606/86 A |
| 2008/0045970 A1 * | 2/2008 | Saidha | A61B 17/8615 606/104 |
| 2008/0082103 A1 * | 4/2008 | Hutton | A61B 17/7004 606/272 |
| 2008/0125817 A1 * | 5/2008 | Arnett | A61B 17/7002 606/319 |
| 2008/0154308 A1 | 6/2008 | Sherman et al. | |
| 2008/0183214 A1 * | 7/2008 | Copp | A61B 17/7005 606/265 |
| 2008/0319477 A1 * | 12/2008 | Justis | A61B 17/7089 606/232 |
| 2009/0171391 A1 * | 7/2009 | Hutton | A61B 17/7032 606/246 |
| 2009/0216280 A1 * | 8/2009 | Hutchinson | A61B 17/88 606/279 |
| 2010/0222828 A1 * | 9/2010 | Stad | A61B 17/8891 606/86 A |
| 2011/0087293 A1 * | 4/2011 | Ferreira | A61B 17/708 606/265 |
| 2011/0152942 A1 * | 6/2011 | Oh | A61B 17/7002 606/279 |
| 2012/0271355 A1 * | 10/2012 | Steele | A61B 17/7008 606/264 |
| 2013/0096635 A1 * | 4/2013 | Wall | A61B 17/7085 606/305 |
| 2013/0103096 A1 * | 4/2013 | Miller | A61B 17/7032 606/305 |
| 2013/0245702 A1 * | 9/2013 | McBride | A61B 17/7076 606/305 |
| 2014/0039567 A1 * | 2/2014 | Hoefer | A61B 17/708 606/86 A |
| 2014/0088647 A1 * | 3/2014 | Baynham | A61B 17/7004 606/246 |
| 2014/0277200 A1 * | 9/2014 | Parker | A61B 17/7076 606/86 A |
| 2015/0105831 A1 * | 4/2015 | Yim | A61B 17/7091 606/86 A |
| 2015/0127054 A1 * | 5/2015 | Tsuang | A61B 17/7032 606/267 |
| 2015/0351810 A1 * | 12/2015 | Lindner | A61B 17/7032 606/278 |
| 2015/0359571 A1 * | 12/2015 | Biedermann | A61B 17/7076 606/246 |
| 2016/0022317 A1 * | 1/2016 | Kraus | A61B 17/708 606/267 |
| 2016/0051285 A1 | 2/2016 | Gleason | |

OTHER PUBLICATIONS

Synthes Cannulated Pangea System Technique Guide, © 2007 Synthes, Inc., West Chester, PA.

Mark Peterson, M.D., Frank Phillips, M.D., William Taylor, M.D., NuVasive DBR Technique Guide, © 2005 NuVasive, Inc., San Diego, CA.

Abbott PathFinder Surgical Technique Guide, Oct. 2008, 1100-0005-MCK Rev H per DCR 6005, Austin, TX.

Kevin T. Foley, M.D., Medtronic Sextant Technique Guide, © 2002 Medtronic Sofamor Danek USA, Memphis, TN.

D. Greg Anderson, M.D., Robert Heary, M.D., Carl Lauryssen, M.D., and Tony Tannoury, M.D., DePuy Viper2 Surgical Tecnhique Guide, May 2008, MIO4-03-000, JC/UM, Raynham, MA.

Biomet Ballista Surgical Technique Guide, © 2008 Biomet, Inc., Parsippany, NJ.

* cited by examiner

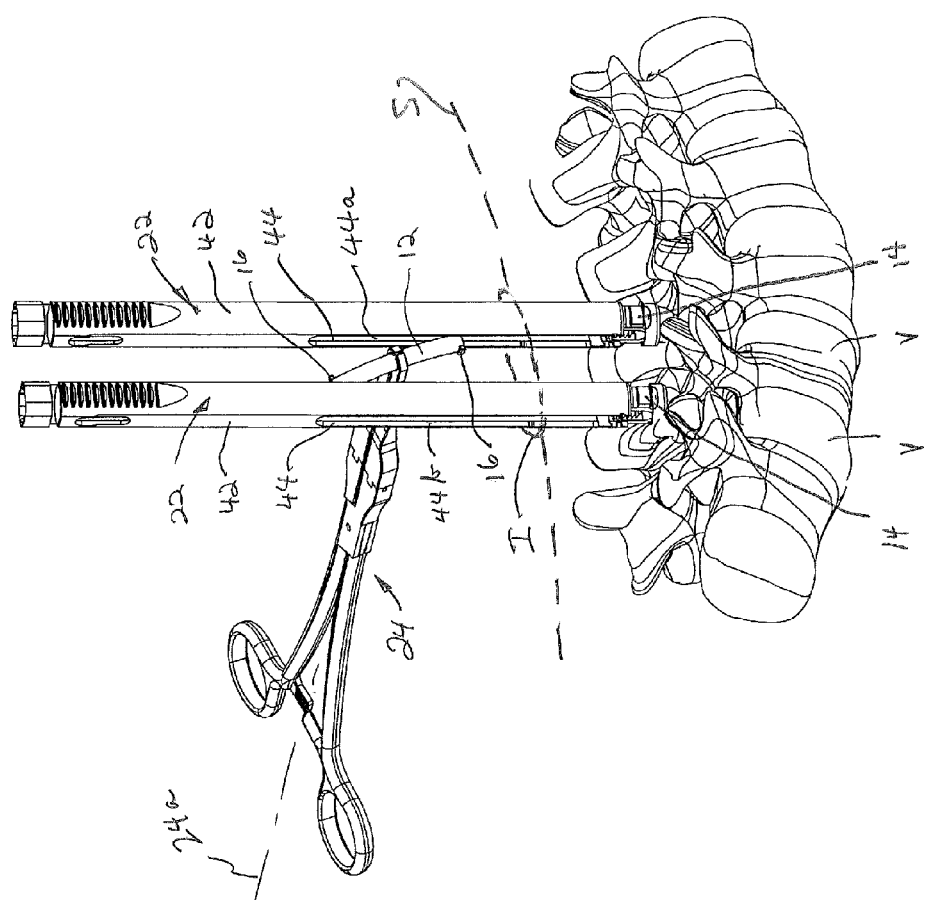

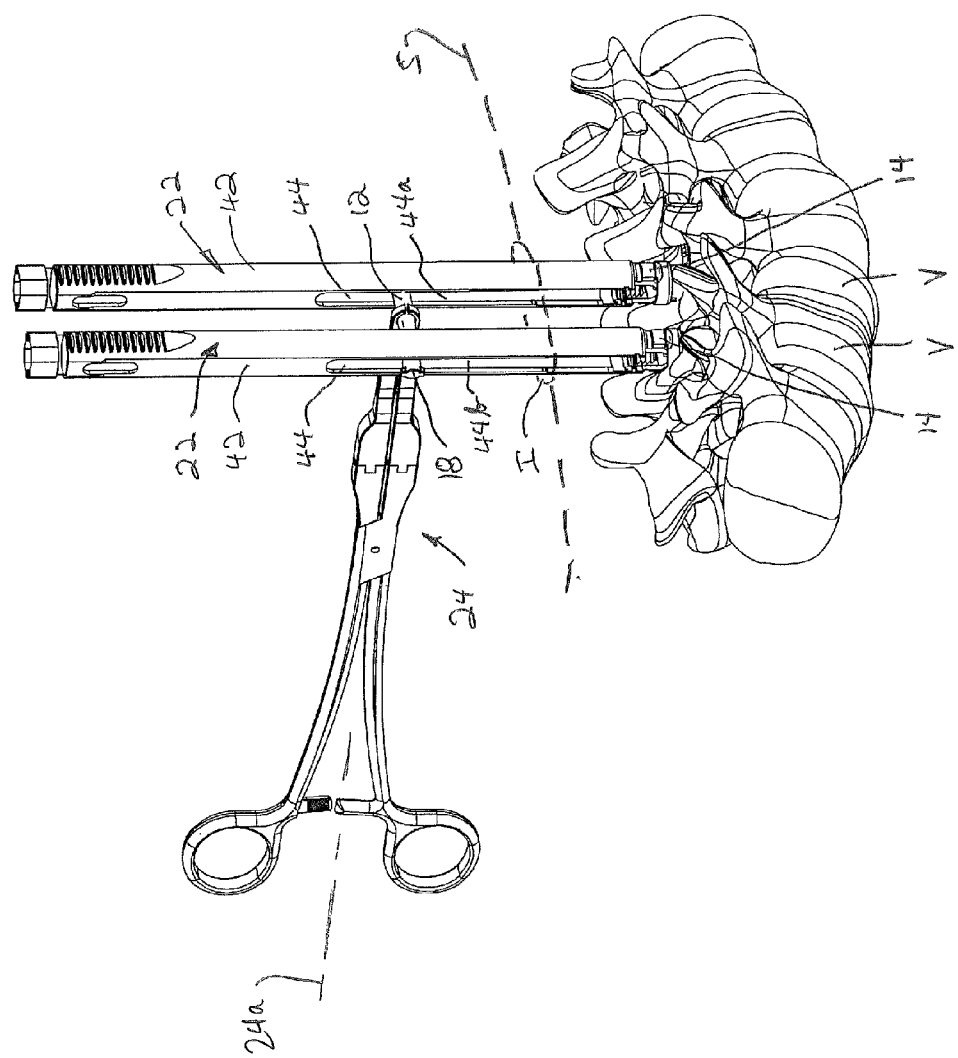

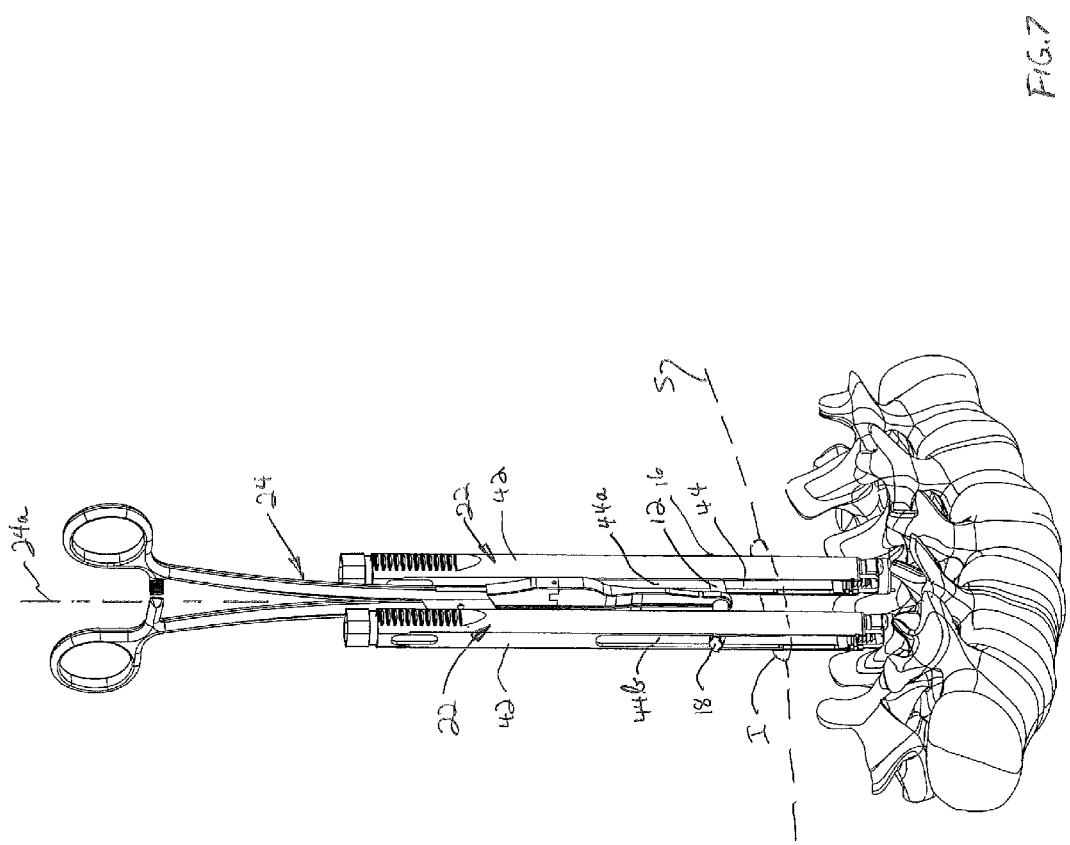

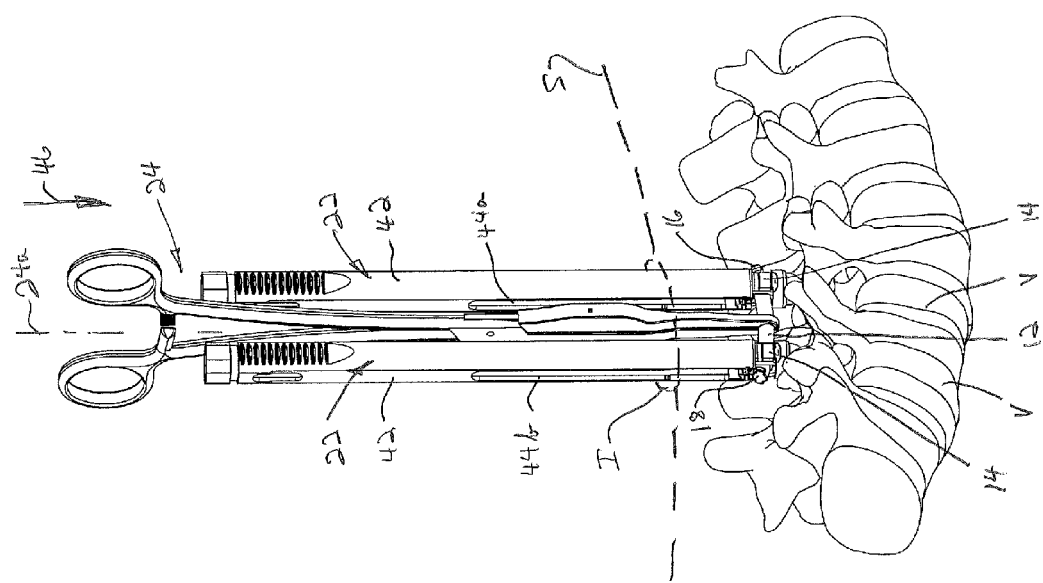

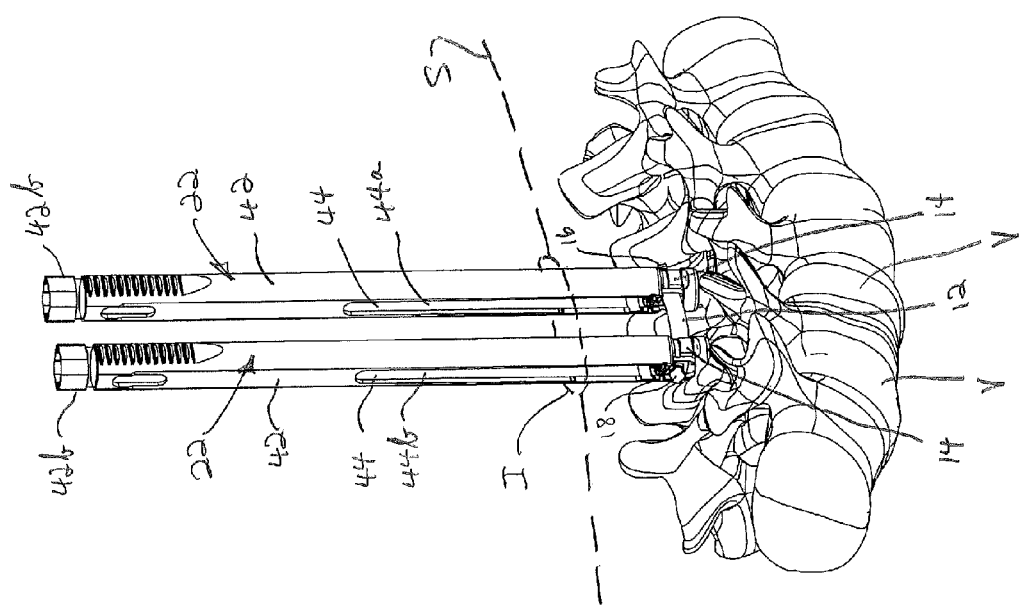

US 9,439,692 B1

MINIMALLY INVASIVE SPINAL FIXATION SYSTEM AND METHOD THEREFOR

FIELD OF THE INVENTION

The present disclosure contemplates a spinal fixation system and more particularly instrumentation and methods for minimally invasively introducing a spinal fixation system into a patient.

BACKGROUND OF THE INVENTION

In the past spinal fixation systems have been implanted in open procedures involving relatively large incisions through the patient's tissue with significant muscle retraction. More recent procedures have been developed to introduce spinal fixation systems in a minimally invasive manner. One technique known as the Sextant® System is described in U.S. Pat. No. 6,530,929, issued to Justis, et al. In the '929 patent, separate incisions are made for introducing respective pedicle screws each attached to a tubular extension extending outwardly from the patient through each incision. A pivot arm coupled to the extensions introduces an elongate rod through another separate incision remote from the incisions receiving the extensions. The pivot arm urges the rod beneath the skin and into the pedicle screws for fixation. Other minimally invasive systems such as that shown in U.S. Pat. No. 7,306,603 issued to Boehm, Jr. et al. utilize tubular pedicle screw extensions to place a rod longitudinally through the extension into one of the pedicle screws. The rod is then pivoted about the pedicle screw through an incision between the pedicle screws to the second pedicle screw. Others still employ systems such as that shown in U.S. Pat. No. 7,250,052 issued to Landry et al. wherein slots in the screw extensions are used to guide a rod between the extensions through a single incision into position in two or more pedicle screws. Yet others provide spinal fixation systems as described in U.S. Pat. No. 8,142,437 (the '437 Patent), issued to McLean et al., and assigned to the same assignee as the subject invention. In the '437 patent, a rod introducer is provided for percutaneously inserting a connecting rod into slots of the screw extensions and into the yokes of the bone screws.

Yet despite advances in spinal fixation devices and techniques, there is still desire for implants, instruments and procedures for minimally invasively placing spinal fixation systems that are relatively simple and easy to use and that provide for enhanced assurance of rod introduction, connection to spinal implants and maintenance of rod position in the spinal fixation system.

SUMMARY OF THE INVENTION

It is an object of the present invention to provide an improved minimally invasive spinal fixation system and method of attaching a spinal fixation system to a spine of a patient.

DESCRIPTION OF THE FIGURES

FIGS. 5-9 are top perspective views illustrating the sequence of the procedure for implanting the minimally invasive spinal fixation system of FIG. 1.

DESCRIPTION OF THE EMBODIMENTS

Figure 1:
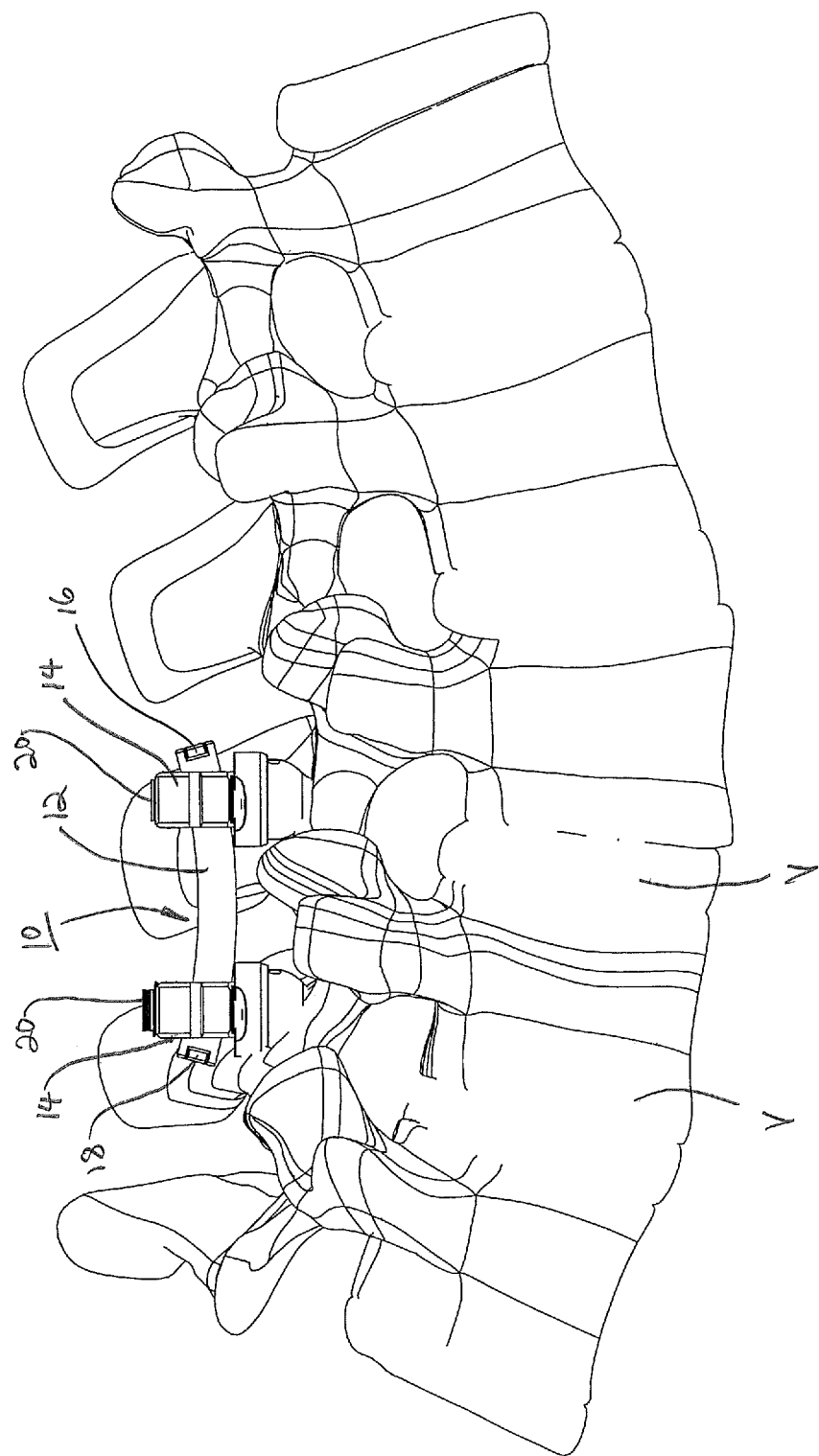
FIG. 1 is a representation of a portion of a patient's spine instrumented with a spinal fixation system in accordance with one arrangement of the subject invention.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring FIG. 1, a minimally invasive spinal fixation system 10 as shown spans successive vertebrae V of the spine. An elongated connecting element 12 extends along the length of the fixation system 10 and provides an anchor point for connecting each vertebra V to the fixation system 10. Connecting element 12 is typically contoured, as will be described, to approximate the normal curvature of the spine for the particular instrumented spinal segments, which may include lordosis or kyphosis. Anchor devices 14 are provided for connecting the vertebral bodies V to connecting element 12. These anchor devices 14 may include hooks, bolts, screws or other means for engaging a vertebra. For the purpose of the present arrangement, anchor device 14 is a bone screw, such as a pedicle screw shown in FIG. 3. However, it should be appreciated that the instrumentation and procedures disclosed herein may be implemented with other types of anchor devices, such as a hook engaged to the lamina of a vertebra for instance. As illustrated, fixation system 10 is located ipsilaterally on one side of the spine. Another similar fixation system may be located ipsilaterally on the other side of the spine. Connecting element 12 includes a pair of location tabs 16 and 18 for positioning connecting element 12 to the pedicle screws 14, as will be detailed. Locking elements, such as set screws 20 may be used to securely fasten connecting element 12 to pedicle screws 14 upon completion of the procedure.

Figure 2:
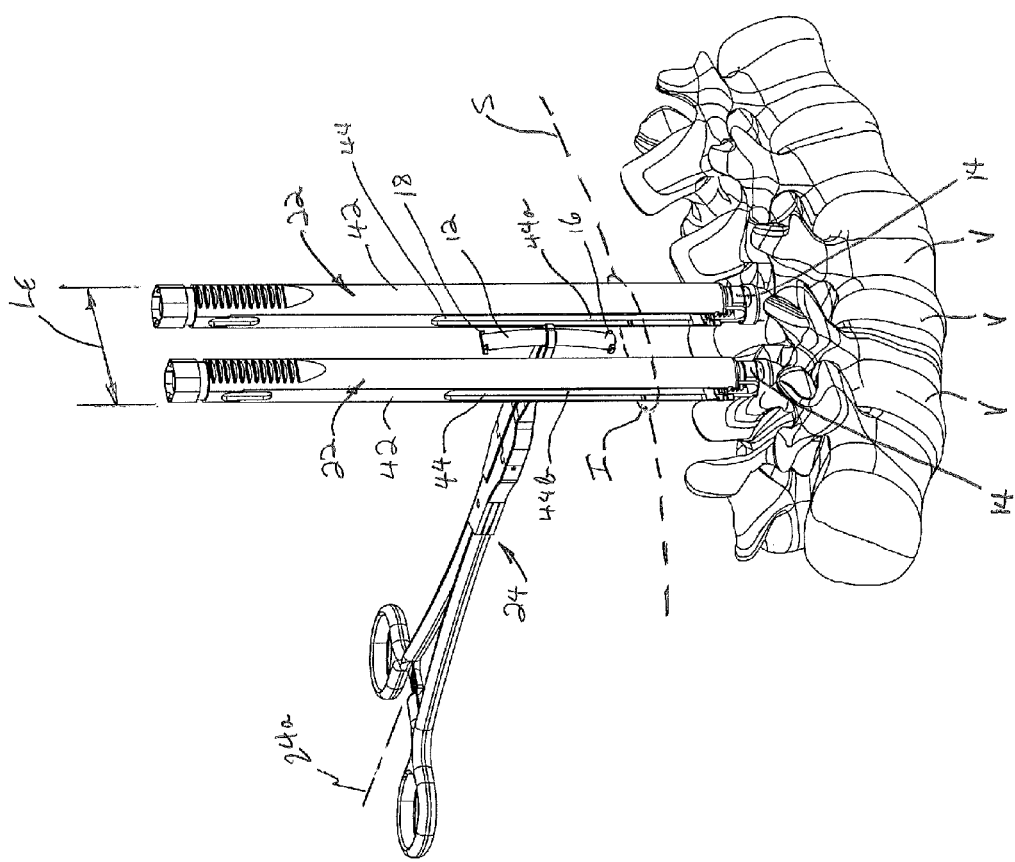
FIG. 2 is a top perspective view of instrumentation disclosed herein used to minimally invasively introduce an elongated connecting element in the spinal fixation system of FIG. 1.

Turning now to FIG. 2, the components of the instrumentation disclosed herein are depicted. In particular, two bone screw extension assemblies 22 are engaged to two spaced vertebrae V in preparation for a single-level fixation of the spine. Elongate connecting element 12 is configured to be attached to pedicle screws 14 to connect each vertebra V. When the construct is complete, connecting element 12 will be locked to each of the screws 14 by a set screw 20, as illustrated in FIG. 1. As shown in FIG. 2, each of the bone screw extension assemblies 22 is sized to be accessible outside the patient's skin S. The patient's skin or fascia is depicted as a phantom line S for illustrative purposes only, with the understanding that the level of the fascia relative to the fixation location on the vertebral bodies will vary from patient to patient. The instruments further include a holder 24 that is used to introduce the connecting element 12 to the pedicle screws 14, as will be set forth below. The nature and manner of operation of these and other instruments are described herein.

Figure 3:
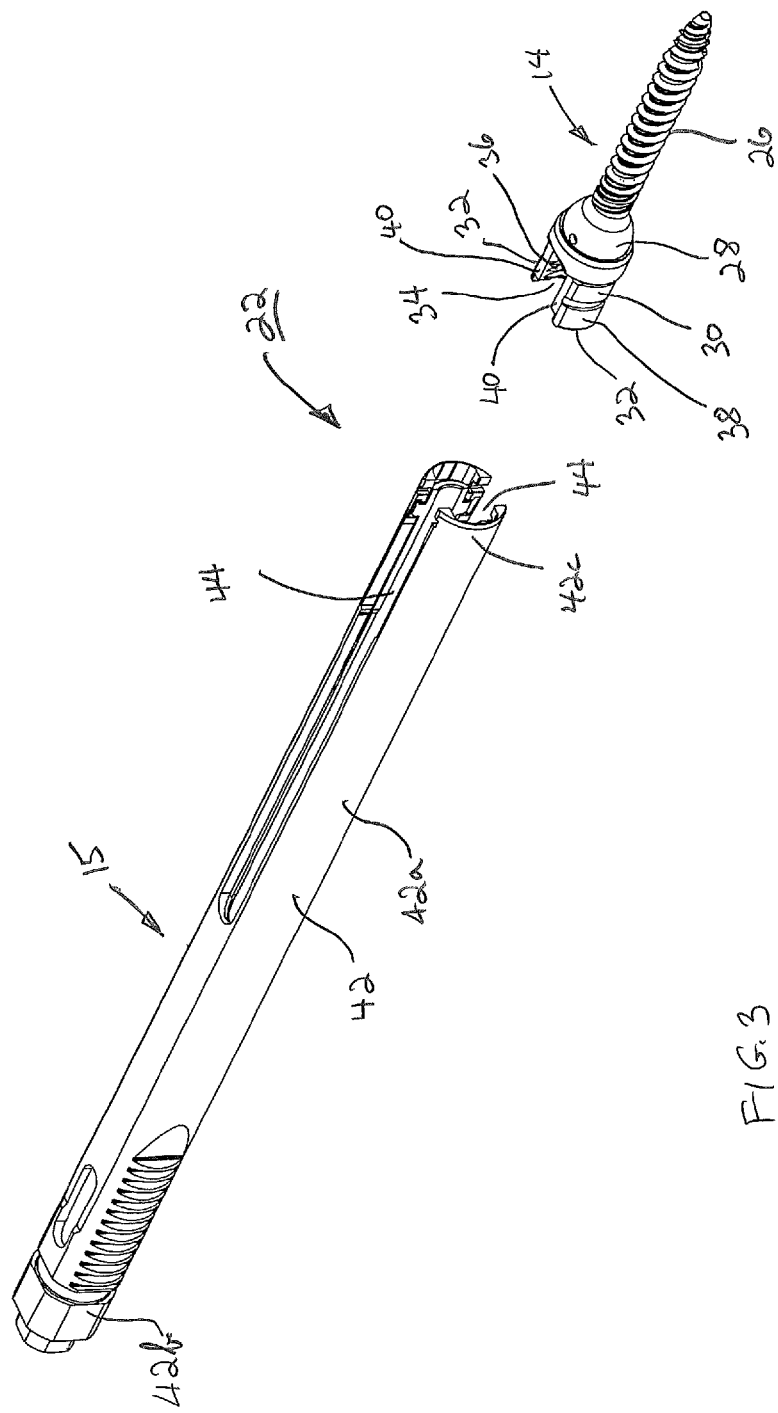
FIG. 3 is an exploded perspective view of a bone screw extension assembly used in the instrumentation of FIG. 2, including a bone screw and a bone screw extension.

Referring now to FIG. 3, further details of the bone screw extension assembly 22 are described. Bone screw extension assembly 22 includes pedicle screw 14 and an elongate bone screw extension 15. Looking first at pedicle screw 14, pedicle screw 14 includes a shaft 26 that carries threads configured to engage vertebral bone, and is particularly threaded for engagement within the pedicle of the vertebra V. The pedicle screw 14 further includes a head 28 by which threaded shaft 26, and ultimately the vertebra V, is fastened to connecting element 12. In particular, head 28 supports a yoke 30 that is generally U-shaped to receive the connecting element 12 therein, as depicted in FIG. 1. In a preferred arrangement pedicle screw 14 is a multi-axial screw wherein yoke 30 is articulatingly attached to the threaded shaft 26 so that the yoke 30 can adopt a range of spherical angles relative to the threaded shaft 26. Thus, the yoke 30 can articulate relative to the threaded shaft 26 attached to the vertebra V so that the yoke 30 can be aligned to properly receive the connecting element 12.

Still referring to FIG. 3, yoke 30 includes opposed upstanding arms 32 that are separated to define a slot 34 therebetween. The slot 34 has a width between the spaced arms 32 that is sized and configured to relatively snugly receive a portion of the connecting element 12 therein. For example, where a connecting element 12 is formed to have a connecting rod 12d of substantially circular cross-section having a diameter D (FIG. 4D) of approximately 0.217 in (5.5 mm), slot 34 may have a width of approximately 0.223 in. Arms 32 of yoke 30 include facing interior surfaces 36 which define internal threads. The threads are configured to mate with the set screw 20 to clamp connecting rod 12 within the yoke 30 and for final fixation of the spinal fixation system 10. The upstanding arms 32 further include an exterior surface 38 that is partially cylindrical and has generally flat exterior surfaces 40 on opposite sides of the slot 34.

As thus far described, pedicle screw 14 is generally similar to the multi-axial pedicle screw described in commonly owned U.S. Pat. No. 8,142,437 (the '437 Patent), entitled "System for Percutaneously Fixing a Connecting Rod to a Spine", issued to McLean et al. on May 27, 2012, the entire disclosure of which is incorporated herein by reference. For the purposes of the present disclosure, pedicle screw 14 may be constructed as disclosed in the '437 Patent, although it is understood that other bone screw or multi-axial fastener configurations may be implanted using the instruments and procedures disclosed herein.

With reference still to FIG. 3, elongate extension 15 includes an elongate hollow tubular member 42 having a perimetric sidewall 42a that defines a hollow interior extending axially through tubular member 42 from a proximal end 42b to a distal end 42c. Distal end 42c is sized to be relatively snugly received about the exterior surface 38 of yoke 30. Perimetric sidewall 42a further defines a pair of opposing elongate slots 44 extending axially through sidewall 42a diametrically apart in communication with the hollow interior of tubular member 42. Slots 44 each have a width that is sized to respectively pass tabs 16 and 18 of connecting element 12 through tubular member 42 when oriented in one direction and to prevent passage when connecting element 12 is oriented in a second different orientation, as will be described. In one arrangement, slots 44 each have approximately the same width, which is slightly greater than but not less than the width of slot 34 of yoke 30. Thus, where slot 34 of yoke 30 has a width of approximately 0.223 in, slots 44 may be formed to each have a width of approximately 0.240 in. In other arrangements, slots 44 may be formed to have different widths, as will be explained below. Slots 44, which open through the distal end 42c, are axially long enough in the proximate direction to extend above the skin line S so that tabs 16, 18 of connecting element 12 may be passed transversely through bone screw extension assemblies 22 outside the patient, as explained in more detail herein. In some arrangements, slots 44 may be formed to also open through the proximal end 42b so that connecting element 12 may be introduced from the top.

Upon releasable engagement to pedicle screw 14, slots 44 are aligned and in communication with the slot 34 in yoke 30. Once extension 15 is attached to pedicle screw 14 to form bone screw extension assembly 22, tubular member 42 and yoke 30 are jointly rotatably manipulable upon rotation of tubular member 42 relative to threaded shaft 26 such that slot 34 together with aligned extension slots 44 may be oriented in a position for receipt of connecting element 12 after threaded shaft 26 is attached to vertebra V, as will be described. As thus far described, extension 15 is generally similar to the bone screw extension described in the '437 Patent and is releasably engaged to pedicle screw 14 in a similar manner as disclosed in the '437 Patent. It should be appreciated, however, that extension 15 may be defined by a pair of spaced extensions that are releasably attached to the respective yoke arms 32 by a frangible breakoff section, the spacing between each such extension defining slots 44.

Figure 4A:
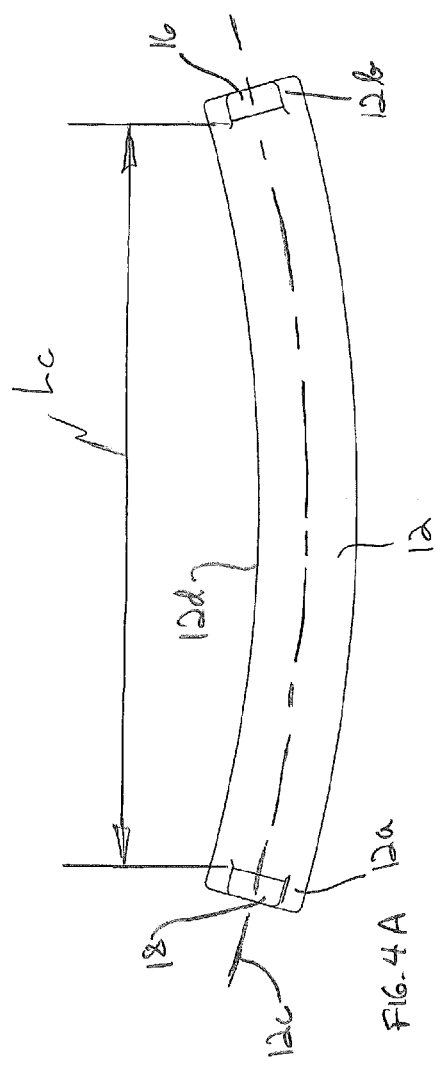
FIGS. 4A, 4B and 4C are side elevation, end and top views respectively of the connecting element shown in FIG. 1.
Figure 4B:
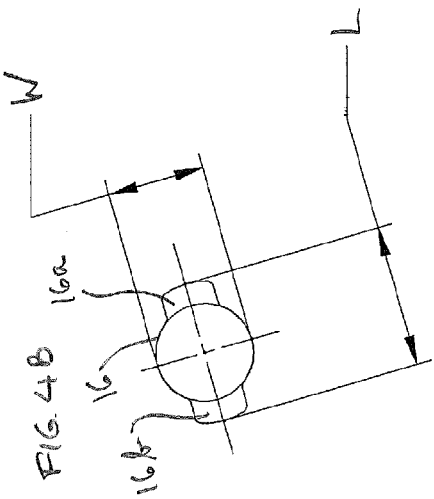
Figure 4C:
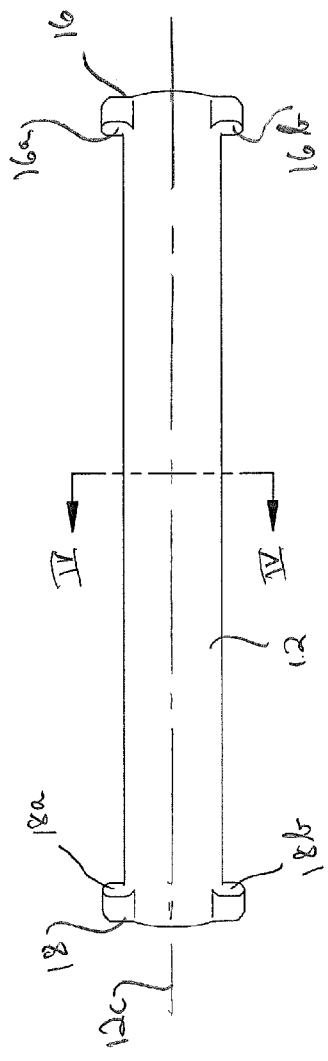
Figure 4D:
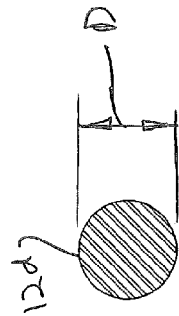
FIG. 4D is cross-section of the connecting element as shown along viewing line IV-IV of FIG. 4C.

Turning now to FIGS. 4A-D, further the details of connecting element 12 are described. Connecting element 12 is elongate having opposite spaced ends 12a and 12b and a longitudinal axis 12c extending centrally therethrough. First location tab 16 is adjacent to one end 12a and projects from connecting element 12 transversely to longitudinal axis 12c. Second location tab 18 is adjacent to the other opposite end 12b and also projects from connecting element 12 transversely to longitudinal axis 12c. Connecting element 12 defines a length $L_C$ extending between tabs 16 and 18 as shown in FIG. 4A. In one arrangement, tabs 16 and 18 are substantially identical and are located directly at the ends 12a and 12b, respectively. Tabs 16 and 18 may, however, be shaped differently from each other, and may also be spaced inwardly of the ends 12a and 12b. As noted hereinabove, connecting element 12 may be contoured to approximate the normal curvature of the spine for the particular instrumented spinal segments. As such, connecting element may be curved as shown in FIG. 4A, with longitudinal axis 12c following the path of curvature. The portion 12d of connecting element 12 between tabs 16 and 18 is in one arrangement configured as a connecting rod having a substantially circular cross-section with a diameter D, as shown in FIG. 4D. Diameter D is generally constant over the full extent of portion 12d, but in some instances diameter D may vary along the length of portion 12d. In one configuration of connecting element 12, connecting rod portion 12d is formed to have a diameter D of approximately 0.217 in (5.5 mm), it being understood that other diameters may be used. It should also be understood that while the cross-section of portion 12d in one arrangement is substantially circular, other cross-sections, such as rectangular, square, oval and polygonal may be used.

As seen in FIG. 4B, each tab 16 and 18 is formed to be of generally rectangular keyhole configuration, having an overall length L and an overall width W. The corners of tabs 16 and 18 may be curved, smoothed or chamfered. Length L is greater than width W. It should be appreciated, however, that tabs 16, 18 may be formed in other shapes, such as oval, for instance. Preferably, as illustrated in FIG. 4C, tabs 16 and 18 each have two portions 16a, 16b and 18a, 18b that project respectively from connecting element 12 on both sides of axis 12c. In one arrangement, each projecting tab portion 16a, 16b and 18a, 18b includes a generally flat engagement surface. Width W, which defines the minimum extent of tabs 16, 18 transverse to longitudinal axis 12c, is formed to be of dimension approximately the same as the maximum cross-sectional dimension D of rod portion 12d between tabs 16 and 18, as shown in FIG. 4D, and preferably not greater. In the arrangement where the rod portion 12d of connecting element is approximately 0.217 in (5.5 mm) in diameter, width W of each tab 16 and 18 is approximately 0.217 in (5.5 mm). The length L, which defines the maximum extent of tabs 16, 18 transverse to longitudinal axis 12c, is approximately 0.313 in. As such, width W of each tab 16, 18 (0.217 in) is slightly less than the width of extension slots 44 (0.240 in) and yoke slot 34 (0.223) while the length L of each tab 16, 18 (0.313 in) is greater than the width of extension slots 44 (0.240 in) and the width of yoke slot 34 (0.223). Thus, when tabs 16 and 18 are oriented with respect to slots 44 of tubular members 42 such that the tab lengths L extend substantially parallel to the axial direction of slots 44, tabs 16 and 18 may pass through slots 44 since the width W of each tab 16 and 18 is less than the width of each slot 44. However, when tabs lengths L are oriented transversely, such as substantially perpendicularly with respect to slots 44, tabs 16 and 18 cannot pass through slots 44 since the length L of each tab 16 and 18 is greater than the width of each slot 44.

In one arrangement, connecting element 12 is formed as an integral, one piece member wherein tabs 16 and 18 are each attached prior to use. As such, connecting element 12 may be machined, or tabs 16 and 18 may be attached to rod portion 12d by welding or other suitable well-known techniques. Connecting element 12 is formed of titanium in one arrangement, but may also be formed of other suitable biomaterials, such as stainless steel.

Having described the instruments and the components of the minimally invasive spinal fixation system 10, the procedures for ipsilaterally implanting fixation system 10 are described with particular reference to FIGS. 2 and 5-9. In one minimally invasive approach, the pedicles of opposing vertebrae V of the patient are located according to known fluoroscopy or other suitable imaging techniques and a single incision I is formed through the skin S of the patient. Incision I is approximately 25-50 mm in length and may be suitably dilated to form a corridor through the tissue of the patient down to the spine and between the vertebrae V to be instrumented. Guide wires may be used to locate the pedicle of each vertebra to be instrument and to facilitate the subsequent introduction of the instruments and fixation system components. For the single level system shown, a pair of bone screw extension assemblies 22 is formed as described hereinabove with respect to FIG. 3. In a preferred procedure, the trajectory for attaching each bone screw extension assembly 22 to a pedicle is in a direction from posterior medial to anterior lateral. It should be appreciated, however, that the trajectory may also be in the more traditional direction, which is from posterior lateral to anterior medial.

Each bone screw extension assembly 22 is separately and sequentially introduced through the incision I and through the tissue and attached to a respective vertebra V by threadably introducing the threaded shaft 26 of each pedicle screw 14 into the pedicle of each vertebra V. With bone screw extensions assemblies 22 suitably attached to pedicles of vertebrae V, tubular members 42 and an axial extent of slots 44 project exteriorly out from the skin S of the patient, as shown in FIG. 2. Tubular members 42 are each oriented by rotation relative to threaded shafts 26 such that one slot 44a of each pair of slots 44 is placed in generally facing relation to another slot 44a (not shown). Second slots 44b (one of which is shown) of each pair of opposing pairs of slots 44 are disposed adjacent opposite ends of incision I, and are spaced at a distance $L_E$, which is the maximum distance between the outside opposite surfaces of tubular members 42, as depicted in FIG. 2. Distance $L_E$ is greater than the spacing between the two opposing interiorly facing first slots 44a. In some arrangements, slots 44a that face each other may be formed to have widths that are greater than the widths of opposite slots 44b, in a manner to facilitate manipulation of tabs 16, 18 of connecting element 12 through tubular members 42, as will be explained.

In another minimally invasive approach, separate spaced individual incisions may be formed through the skin S of the patient and suitably dilated for individual introduction of a bone screw extension assembly 22. Each separate incision may be approximately 10-20 mm in length. Once each bone extension assembly 22 is attached to a respective pedicle of a vertebra V, the separate incisions may be joined by incising the skin and tissue between the spaced incisions and forming a pathway through tissue down to the surgical site to form a common incision similar to the single incision I. The minimally invasive attachment of bone screw extension assemblies 22 in either the single incision approach or the separate incision approach is more fully described in the '437 Patent, incorporated herein by reference.

After bone screw extension assemblies 22 have been properly attached to vertebra V, distance $L_E$ is effectively measured by a placing a caliper or other suitable measurement instrument into the hollow interior of tubular members 42 along their centerlines. In one arrangement, a connecting element 12 is chosen to have a length $L_C$ that is greater than distance $L_E$. Holder 24, which may be forceps or other suitable holding instrument, is provided for grasping connecting rod 12 generally centrally along rod portion 12d such that tabs 16, 18 project transversely relative to a central axis 24a of holder 24, as shown in FIG. 2. As illustrated in FIG. 2, connecting element 12 is initially placed between bone screw extension assemblies 22 with its longitudinal axis oriented generally parallel to tubular members 42 and adjacent to facing slots 44a. In this orientation, central axis 24a of holder 24 is substantially perpendicular to the direction of elongate tubular members 42 projecting outwardly from skin S of the patient and tabs 16, 18 of connecting element 12 are oriented such that their respective lengths L are not transverse to facing slots 44a.

Referring now to FIGS. 5-6, the next step in the procedure is illustrated. Connecting element 12 is manipulated by rotating holder 24 about its central axis 24a causing tabs 16, 18 to enter tubular members 42 by passing through facing slots 44a, as depicted in FIG. 5. Continued rotation of holder 24 about its axis 24a causes tabs 16, 18 to extend through outside slots 44b as shown in FIG. 6. In this stage, tabs 16, 18 are disposed exteriorly adjacent tubular members 42 with the lengths L of tabs 16, 18 being aligned generally parallel to slots 44b. It should be appreciated that if facing slots 42a were formed to have widths greater than opposing slots 44b, the step of manipulating tabs 16, 18 of connecting element 12 through tubular members 42 may be more readily facilitated.

As shown in FIG. 7, connecting element 12 is then rotated by holder 24 such that its central axis 24a lies generally parallel to tubular members 42. In this orientation, the lengths L of tabs 16, 18 are disposed exteriorly of tubular members 42 and transversely across the widths of slots 44b. As such, connecting element is prevented by tabs 16,18 from passing back out from or further through tubular members 42. Holder 24 is then pushed downwardly as shown by arrow 46 in FIG. 8 moving connecting element 12 into the patient though incision I. During the downward movement connecting element 12 is guided without resort to fluoroscopy or other imaging techniques by and along slots 44 of tubular members 42 until connecting element 12 is received by pedicle screws 14. Upon proper seating as shown in FIG. 9, a portion of connecting element 12 interiorly adjacent each tab 16, 18 will reside in slots 34 of yokes 30 of the respective pedicle screws 14. Tabs 16, 18 lying exteriorly of tubular members 42, secure the position of connecting element 12 relative to pedicle screws 14. With holder 24 holding the connecting element 12 in place, set screws 20 are introduced into the hollow interior of tubular members 42 through the proximal end 42b by a screwdriver or other suitable tool to securely fasten connecting element 12 to pedicle screws 14 upon completion of the procedure. Holder 24 is then separated from connecting element 12 and removed from the surgical site. Extensions 22 are then released from each of the pedicle screws 14 resulting in the fixation structure 10 shown in FIG. 1.

In an alternative arrangement, after distance $L_E$ is determined, a connecting element 12 is chosen to have a length $L_C$ that is less than distance $L_E$. Tabs 16, 18 are formed in the same size and configuration as described above. Connecting element 12 is manipulated by holder 24 in a manner as described above with respect to FIGS. 2, 5-6 to pass tabs 16, 18 through slots 44. The proximal ends 42b of each tubular member 42 may be moved angularly closer to each other to assist in the manipulation process. Upon rotation of holder 24 such that holder axis 24a is in the vertical position as depicted in FIG. 7, the lengths L of tabs 16, 18 will extend transversely across outside slots 44b with projecting tab portions 16a, 16b and 18a, 18b engaging the exterior surfaces of respective tubular members 42 adjacent slots 44b. As connecting element 12 is moved through the incision I along slots 44 as shown in FIG. 8, the sliding engagement of projecting tab portions 16a, 16b and 18a, 18b against tubular members 42 will cause the distal ends 42a of tubular members 42 to move closer to each other. Such movement will in turn cause pedicle screws 14 as well as the attached vertebrae V to move closer to each other, thereby resulting in tension in rod portion 12d and compression of the spinal segment. Upon seating the connecting element 12 in pedicle screws 14, projecting tab portions 16a, 16b and 18a, 18b will extend across yoke slots 34 and be in engagement with the flat surfaces 40 of each of the yoke arms 32. As such, compression of the spinal segment will be maintained after the surgical procedure is completed. Connecting element 12 is similarly fastened to pedicle screws 14 with set screws 20 as described hereinabove.

While the minimally invasive system 10, its instruments and implantation techniques have been described herein for a single level, it should be appreciated that fixation system 10 may also be implanted in two or more levels with the components and instruments as described herein. In addition, while the fixation system 10 has been described herein being implanted minimally invasively, it should be understood that a surgeon may also use the described fixation system and instruments in an open procedure, if that is the surgeon's surgical preference.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A minimally invasive method of attaching a spinal fixation system to a spine of a patient, comprising the steps of:

placing a first bone screw extension assembly through an incision, said first bone screw extension assembly comprising a first bone screw including a shaft having a threaded portion and a first yoke articulatingly attached to said shaft, said first yoke including a pair of upstanding opposed arms defining a first slot having a first width therebetween, and a first bone screw extension having a distal end and a proximal end, said first screw extension including a first tubular member defined by a perimetric sidewall having a first pair of opposing slots through said sidewall in alignment and communication with said first slot of said first yoke, said first screw extension being releasably engaged to said first yoke for articulation therewith;

attaching said first bone extension assembly to said spine by threadably introducing said threaded portion of said shaft of said first bone screw into a first vertebra, a portion of said first tubular member and said first pair of slots being disposed exteriorly of said patient;

placing a second bone screw extension assembly through an incision, said second bone screw extension assembly comprising a second bone screw including a shaft having a threaded portion and a second yoke articulatingly attached to said shaft, said second yoke including a pair of upstanding opposed arms defining a second slot having a second width therebetween, and a second bone screw extension having a distal end and a proximal end, said second screw extension including a second tubular member defined by a perimetric sidewall having a second pair of opposing slots through said sidewall in alignment and communication with said second slot of said first second yoke, said second screw extension being releasably engaged to said second yoke for articulation therewith;

attaching said second bone extension assembly to said spine by threadably introducing said threaded portion of said shaft of said second bone screw into a second vertebra spaced from said first vertebra, a portion of said second tubular member and said second pair of slots being disposed exteriorly of said patient;

orienting said first tubular member and said second tubular member such that a first slot of said first pair of slots is in generally facing relation to a first slot of said second pair of slots;

placing a connecting element between said first tubular member and said second tubular member outside said patient, said connecting element having first and second opposite ends and a longitudinal axis extending therebetween, said connecting element including a first tab adjacent to said first end and projecting from said connecting element transversely to said longitudinal axis and a second tab adjacent to said second end and projecting from said connecting element transversely to said longitudinal axis; and manipulating said connecting element from between said first tubular member and said second tubular member such that said first tab is positioned adjacent to an exterior surface of said first tubular member with a portion of said connecting element adjacent said first tab extending through said first pair of opposing slots and with said first tab extending across a second slot of said first pair of slots and such that said second tab is positioned adjacent to an exterior surface of said second tubular member with a portion of said connecting element adjacent said second tab extending through said second pair of opposing slots and with said second tab extending across a second slot of said second pair of slots.

2. The minimally invasive method of claim 1, wherein said manipulating step is practiced by initially extending said first tab from said position between said first tubular member and said second tubular member through said first pair of slots of said first tubular member then extending said second tab through said second pair of slots of said second tubular member and then rotating said connecting element such that said first tab extends across the second slot of said first pair of slots and such that said second tab extends across the second slot of said second pair of slots.

3. The minimally invasive method of claim 2, wherein a single incision is formed through which said first bone screw extension assembly and said second bone screw extension assembly are placed for attachment respectively to said first and second vertebra.

4. The minimally invasive method of claim 3, further including the step of moving said connecting element into said incision along said first pair of slots and said second pair of slots until said connecting rod is received in said first slot of said first yoke and said second slot of second yoke.

5. The minimally invasive method of claim 4, wherein said connecting element is selected to have a length between said first tab and said second tab such that said first tab engages an exterior surface of said first tubular member and said second tab engages an exterior surface of said second tubular member.

6. The minimally invasive method of claim 2, wherein a first incision is formed though which said first bone screw extension assembly is placed and wherein a second separate incision is formed though which said second bone screw extension assembly is placed, said first incision and said second incision being joined to form a common incision before said connecting element is placed.

7. A minimally invasive method of attaching a spinal fixation system to a spine of a patient, comprising the steps of:
  forming an incision through tissue of a patient and creating an access path through said incision to said spine;
  placing a first bone screw extension assembly through said incision, said first bone screw extension assembly comprising a first bone screw including a shaft having a threaded portion and a first yoke articulatingly attached to said shaft, said first yoke including a pair of upstanding opposed arms defining a first slot having a first width therebetween, and a first hollow bone screw extension having a distal end and a proximal end, said first screw extension including a first tubular member defined by a perimetric sidewall and a hollow interior, said first screw extension having a first pair of opposing slots through said sidewall opening at said distal end and being in alignment and communication with said first slot of said first yoke, said first screw extension being releasably engaged to said first yoke for articulation therewith;
  attaching said first bone extension assembly to said spine by threadably introducing said threaded portion of said shaft of said first bone screw into a first vertebra, a portion of said first tubular member and said first pair of slots being disposed exteriorly of said patient;
  placing a second bone screw extension assembly through said incision, said second bone screw extension assembly comprising a second bone screw including a shaft having a threaded portion and a second yoke articulatingly attached to said shaft, said second yoke including a pair of upstanding opposed arms defining a second slot having a second width therebetween, and a second hollow bone screw extension having a distal end and a proximal end, said second screw extension including a second tubular member defined by a perimetric sidewall and a hollow interior, said second screw extension having a second pair of opposing slots through said sidewall opening at said distal end and being in alignment and communication with said second slot of said first second yoke, said second screw extension being releasably engaged to said second yoke for articulation therewith;
  attaching said second bone extension assembly to said spine by threadably introducing said threaded portion of said shaft of said second bone screw into a second vertebra spaced from said first vertebra, a portion of said second tubular member and said second pair of slots being disposed exteriorly of said patient;
  orienting said first tubular member and said second tubular member such that one slot of said first pair of slots is in generally facing relation to one slot of said second pair of slots;
  determining the maximum distance between the exterior surfaces of said first tubular member and said second tubular member and selecting a connecting element to have a length between said first tab and said second tab that is less than said maximum distance,
  placing said connecting element adjacent said first tubular member and said second tubular member from a position outside said patient, said connecting element having first and second opposite ends and a longitudinal axis extending therebetween, said connecting element including a first tab adjacent to said first end and projecting from said connecting element transversely to said longitudinal axis, said first tab being placed adjacent to an exterior surface of said first tubular member, and a second tab adjacent to said second end and projecting from said connecting element transversely to said longitudinal axis, said second tab being placed adjacent to an exterior surface of said second tubular member;
  moving said connecting element through said incision along said first pair of slots and said second pair of slots such that said first tab slides along said exterior surface of said first tubular member and said second tab slides along said exterior surface of said second tubular member to thereby cause the distal ends of said first and second tubular members to move closer to each other and thereby cause compression of the spinal segment between said first vertebra and said second vertebra; and
  continuing to move said connecting element until said connecting element is seated in said first slot of said first yoke and said second slot of second yoke.

8. The minimally invasive method of claim 7, wherein said connecting element between said first tab and said second tab is curved in a plane along and including said longitudinal axis to approximate the normal curvature of the spine between said first vertebra and said second vertebra, wherein each of said first tab and said second tab projects outwardly from said plane, and wherein during said placing step said connecting element is oriented such that said curvature is in the same direction as said normal curvature of the spine between said first vertebra and said second vertebra.

9. The minimally invasive method of claim 7, wherein upon seating of said connecting element in said first slot of said first yoke and said second slot of second yoke, said first tab extends across said first slot and in engagement with each of the arms of said first yoke, and said second tab extends across said second slot and in engagement with each of the arms of said second yoke.

10. The minimally invasive method of claim 7, wherein said first bone screw extension assembly and said second bone screw extension assembly are each attached respectively to a pedicle of said first vertebra and said second vertebra in a direction from posterior medial to anterior lateral.

11. The minimally invasive method of claim 7, wherein said first bone screw extension assembly and said second bone screw extension assembly are each attached respectively to a pedicle of said first vertebra and said second vertebra in a direction from posterior lateral to anterior medial.

* * * * *